(12) United States Patent
Lee et al.

(10) Patent No.: US 9,085,670 B2
(45) Date of Patent: Jul. 21, 2015

(54) PLASTICIZER, PLASTICIZER COMPOSITION, HEAT-RESISTANT RESIN COMPOSITION AND METHOD FOR PREPARING THE SAME

(71) Applicant: LG CHEM, LTD., Seoul (KR)

(72) Inventors: Mi Yeon Lee, Daejeon (KR); Dong Hyun Ko, Daejeon (KR); Hyun Kyu Kim, Daejeon (KR); Da Won Jung, Daejeon (KR); Gyu Il Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 14/052,100

(22) Filed: Oct. 11, 2013

(65) Prior Publication Data

US 2014/0096703 A1    Apr. 10, 2014

Related U.S. Application Data

(63) Continuation of application No. PCT/KR2013/004433, filed on May 21, 2013.

(30) Foreign Application Priority Data

Oct. 10, 2012  (KR) .......................... 10-2012-0112401
Oct. 10, 2012  (KR) .......................... 10-2012-0112406

(51) Int. Cl.
C08K 5/12           (2006.01)

(52) U.S. Cl.
CPC .......................... *C08K 5/12* (2013.01)

(58) Field of Classification Search
CPC .......................................................... C08K 5/12
USPC .......................................................... 524/297
See application file for complete search history.

(56) References Cited

U.S. PATENT DOCUMENTS

| | | | |
|---|---|---|---|
| 4,675,434 A | 6/1987 | Uhm et al. | |
| 4,929,749 A | 5/1990 | Gupta et al. | |
| 5,624,987 A | 4/1997 | Brink | |
| 2003/0014948 A1 | 1/2003 | Gott | |
| 2006/0167151 A1 | 7/2006 | Grass et al. | |
| 2007/0105999 A1 | 5/2007 | De Munck et al. | |
| 2008/0058450 A1* | 3/2008 | Stimpson et al. | 524/296 |
| 2010/0120910 A1 | 5/2010 | Dierker | |
| 2010/0305250 A1* | 12/2010 | Colle et al. | 524/112 |
| 2010/0310891 A1 | 12/2010 | Godwin | |
| 2013/0225851 A1 | 8/2013 | De Munck et al. | |

FOREIGN PATENT DOCUMENTS

| | | |
|---|---|---|
| CN | 101679708 A | 3/2010 |
| CN | 101878260 A | 11/2010 |
| JP | 60-172945 A | 9/1985 |
| JP | 03-56446 A | 3/1991 |
| JP | 04-106145 A | 4/1992 |
| JP | 09-151273 A | 6/1997 |
| JP | 2003-238479 A | 8/2003 |
| JP | 2006-188521 A | 7/2006 |
| JP | 2007-504105 A | 3/2007 |
| JP | 2011-006565 A | 1/2011 |
| KR | 10-957134 B1 | 5/2010 |
| WO | 2008/140177 A1 | 11/2008 |
| WO | 2009070398 A1 | 6/2009 |

* cited by examiner

*Primary Examiner* — Ling Choi
*Assistant Examiner* — Lanee Reuther
(74) *Attorney, Agent, or Firm* — McKenna Long & Aldridge, LLP

(57) ABSTRACT

Disclosed are a plasticizer that, when used for a heat-resistant resin composition, improves elongation retention, enhances aging resistance and heat resistance, and exhibits superior tensile strength, tensile strength retention, heating loss or the like before and after heating, thus contributing to enhancement in physical properties of the heat-resistant resin, a plasticizer composition, a heat-resistant resin composition and a method for preparing the same.

5 Claims, No Drawings

PLASTICIZER, PLASTICIZER COMPOSITION, HEAT-RESISTANT RESIN COMPOSITION AND METHOD FOR PREPARING THE SAME

This application is a bypass continuation of International Application No. PCT/KR2013/004433, filed on May 21, 2013, which claims priority to Korean Patent Application Nos. 10-2012-0112401, filed on Oct. 10, 2012 and 10-2012-0112406, filed on Oct. 10, 2012, all of which are hereby incorporated by reference in their entirety for all purposes as if fully set forth herein.

TECHNICAL FIELD

The present invention relates to a plasticizer, a plasticizer composition, a heat-resistant resin composition and a method for preparing the same. More specifically, the present invention relates to a plasticizer that, when used for a heat-resistant resin composition, improves elongation retention, enhances aging resistance and heat resistance, and exhibits superior tensile strength, tensile strength retention, heating loss or the like before and after heating, thus contributing to enhancement in physical properties of the heat-resistant resin, a plasticizer composition and a heat-resistant resin composition and a method for preparing the same.

BACKGROUND ART

In general, plasticizers are based on corresponding esters produced through reaction of alcohols with polycarboxylic acids such as phthalic acid or adipic acid. Examples of commercially essential plasticizers include adipates of $C_8$, $C_9$ and $C_{10}$ alcohols such as di(2-ethylhexyl)adipate, diisononyl adipate and diisodecyl adipate; and phthalates of $C_8$, $C_9$ and $C_{10}$ alcohols such as di(2-ethylhexyl)phthalate, diisononyl phthalate and diisodecyl phthalate.

Meanwhile, plasticizers should be suitably selected according to UL (Underwriters Laboratories) heat resistance grade in order to produce wires (cables), automobile sheets and the like requiring heat resistance as a physical property.

For example, in case of PVC compounds for UL cables, a plasticizer, a filler, a flame retardant, a heat stabilizer or the like is blended with a PVC resin according to tensile strength, elongation, cold resistance and the like which are properties required to meet UL cable standards (grades).

The type of plasticizer used depends on heat-resistance grade. Specifically, plasticizers such as dioctyl phthalate (DOP), diisodecyl phthalate (DIDP) and diisononyl phthalate (DINP) are commonly used for 80 to 90° C. heat-resistance grade, and plasticizers such as trioctyl trimellitate (TOTM) and triisononyl trimellitate (TINTM) are used for 105° C. heat-resistance grade.

However, these plasticizers have superior heat resistance, but have a disadvantage of poor compatability.

In addition, a resin used also depends on heat-resistance grade of cables. More specifically, inexpensive PVC is generally used for products requiring heat resistance of 105° C. or less, and polyolefins such as polyethylene (PE) and thermoplastic elastomers (TPE) are generally used for products requiring heat resistance of 105 to 150° C.

In particular, for preparation of a polyethylene compound, unlike PVC, addition of a flame retardant is required, since polyethylene does not have flame retardancy, and a cross-linking agent is required for irradiation. That is, the polyethylene compound is prepared by adding carbon black to polyethylene and adding a plasticizer, a cross-linking agent, a flame retardant or the like thereto, followed by stirring and injection molding.

Accordingly, there is still a need for a plasticizer having heat resistance and superior compatability (workability) and a heat-resistant resin composition comprising the same.

DISCLOSURE

Technical Problem

Through extensive and repeated research into heat-resistant plasticizers, the present inventors discovered that a plasticizer composition capable of solving low compatability caused by structural limitations can be obtained by blending a terephthalate compound containing an alkyl group having 10 carbon atoms (hereinafter, referred to as "$C_{10}$") in order to solve low heat resistance of terephthalate plasticizers containing an alkyl group having 8 carbon atoms (hereinafter, referred to as "$C_8$"). The present invention has been completed based on this discovery.

That is, it is one object of the present invention to provide a plasticizer capable of improving physical properties such as heat resistance and compatability required for heat-resistant compounds, when used for a heat-resistant resin composition, a plasticizer composition, a heat-resistant resin composition comprising the same and a method for preparing the same.

It is another object of the present invention to provide a plasticizer composition wherein a $C_{10}$ terephthalate compound is incorporated in order to solve low heat resistance of $C_8$ terephthalate plasticizers and the $C_{10}$ terephthalate compound is used in combination with dipropyl heptyl phthalate in order to solve low compatability caused by structural limitations during blending, and a method for preparing the same.

Technical Solution

In accordance with one aspect of the present invention, the above and other objects can be accomplished by the provision of a terephthalate plasticizer represented by the following Formula 1.

[Formula 1]

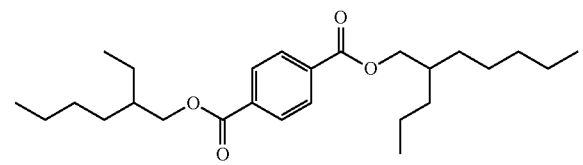

In accordance with another aspect of the present invention, provided is a plasticizer composition comprising: 5 to 60% by weight of the plasticizer of Formula 1; 0.1 to 50% by weight of a terephthalate compound represented by the following Formula 2; and 30 to 85% by weight of a terephthalate compound represented by the following Formula 3.

[Formula 2]

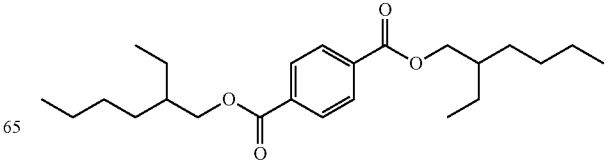

-continued

[Formula 3]

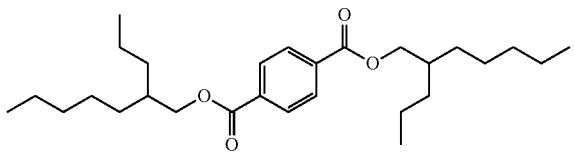

In accordance with another aspect of the present invention, provided is a plasticizer composition comprising: 0.1 to 50% by weight of the plasticizer of Formula 1; 0.1 to 50% by weight of a terephthalate compound represented by the following Formula 2; and 30 to 85% by weight of the terephthalate compound represented by the following Formula 3, wherein the total weight of the plasticizer, the terephthalate compound of Formula 2 and the terephthalate compound of Formula 3 is 100% by weight, the plasticizer composition further comprising 0.1 to 50% by weight of a phthalate compound represented by the following Formula 4.

[Formula 4]

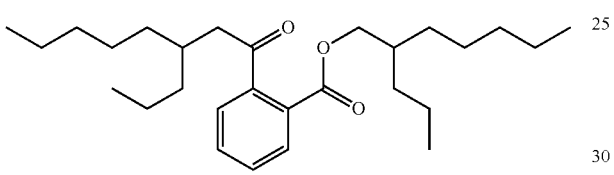

In accordance with another aspect of the present invention, provided is a method for preparing a plasticizer composition comprising:

mixing terephthalic acid with a solvent composed of a mixture of alcohols;

adding a catalyst obtained mixing material, followed by reacting under a nitrogen atmosphere;

removing the unreacted alcohol and neutralizing the unreacted acid; and dehydrating the resulting substance by distillation under reduced pressure, followed by filtering, to obtain a terephthalate composition comprising the terephthalate compound of Formula 1, the terephthalate compound of Formula 2, and the terephthalate compound of Formula 3.

In accordance with another aspect of the present invention, provided is a heat-resistant resin composition comprising 5 to 100 parts by weight of the plasticizer or the plasticizer composition, with respect to 100 parts by weight of a resin selected from ethylene vinyl acetate, polyethylene, polypropylene, polyvinyl chloride, polystyrene, polyurethane and a thermoplastic elastomer.

Hereinafter, the present invention will be described in detail.

First, in one aspect, the present invention provides a terephthalate plasticizer represented by the following Formula 1 as a plasticizer:

[Formula 1]

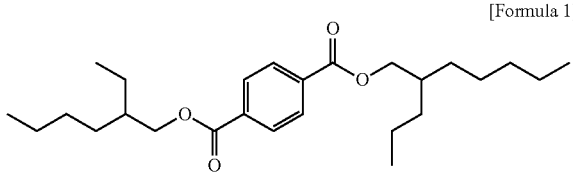

It can be seen that physical properties such as aging resistance, heat resistance, tensile strength, tensile strength retention, elongation retention and heating loss are poor, when the numbers of carbon atoms constituting the plasticizer are 8 and 9, rather than 8 and 10.

In addition, the plasticizer composition of the present invention comprises:

5 to 60% by weight of the plasticizer;

0.1 to 50% by weight of a terephthalate compound represented by the following Formula 2; and 30 to 85% by weight of a terephthalate compound represented by the following Formula 3.

[Formula 2]

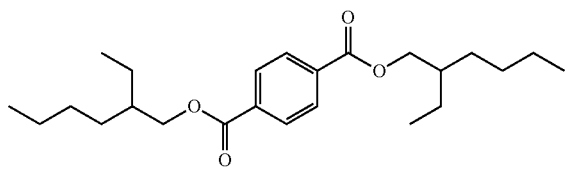

[Formula 3]

It can be seen that physical properties such as aging resistance, heat resistance, tensile strength, tensile strength retention, elongation retention and heating loss are poor, when the numbers of carbon atoms constituting the plasticizer composition are 8 and 9, rather than 8 and 10. When a content of the terephthalate compound represented by Formula 1 is lower than 5% by weight, based on the total weight of the composition, absorption speed of the resin is low and hardness thereof increases, and when the content thereof exceeds 60% by weight, elongation retention and heating loss are not preferred. For example, the content of the terephthalate compound may range from 1 to 35% by weight.

In addition, when the content of the terephthalate represented by Formula 2 is lower than 0.1% by weight, based on the total weight of the composition, absorption speed of the resin is low, and when the content thereof exceeds 50% by weight, migration loss is not preferred. For example, the content of the terephthalate may range from 1 to 35% by weight.

In addition, when the content of the terephthalate represented by Formula 3 is lower than 30% by weight, based on the total weight of the composition, improvement in heat resistance is unsatisfactory, and when the content thereof exceeds 85% by weight, migration loss is not preferred. For example, the content of the terephthalate may range from 64 to 80% by weight.

These plasticizer compositions may be obtained by preparing and blending respective components, or using a mixture blended through esterification of a suitable alcohol mixture with terephthalic acid.

For example, the plasticizer compositions can be simply and efficiently obtained by the following method:

First, terephthalic acid is mixed with a solvent composed of a mixture of alcohols (first step).

Then, a catalyst is added to the resulting mixture, followed by reacting under a nitrogen atmosphere (second step). Then, unreacted alcohol is removed and unreacted acid is neutralized (third step).

Then, the resulting substance is dehydrated by distillation under reduced pressure, followed by filtration, to obtain a terephthalate composition (fourth step).

The solvent composed of a mixture of alcohols used in the first step is a mixture of a $C_{10}$ alcohol selected from 2-propylheptyl alcohol, 4-methyl-2-propyl-1-hexyl alcohol, 5-methyl-2-propyl-1-hexyl alcohol, normaldecyl alcohol and isodecyl alcohol, and a $C_8$ alcohol selected from 2-ethylhexyl alcohol and normaloctyl alcohol. The solvent composed of a mixture of alcohols enables a terephthalate-based composition obtained by adding a $C_{10}$ alcohol having a high molecular weight to exhibit synergetic effect of improved compatability, while taking into consideration the fact that heat resistance is low when a terephthalate-based plasticizer obtained by using $C_8$ alcohol which imparts suitable molecular weight and physical properties to the plasticizer is used as a plasticizer for heat-resistant resins.

Specifically, it is preferable that the solvent composed of a mixture of alcohols comprises 10 to 90% by weight of a $C_{10}$ alcohol such as 2-propylheptyl alcohol and 10 to 90% by weight of a $C_8$ alcohol such as 2-ethylhexyl alcohol, since the terephthalate-based composition satisfies a compositional ratio of 5 to 60% by weight of the terephthalate compound represented by Formula 1, 0.1 to 50% by weight of the terephthalate compound represented by Formula 2 and 30 to 85% by weight of the terephthalate compound represented by Formula 3.

The terephthalic acid may be used in conjunction with a carboxylic acid, a polycarboxylic acid or an anhydride thereof. In particular, a terephthalic acid having a mean particle diameter of 30 to 100 µm, obtained by wet grinding, can reduce reaction time. A desired mean particle diameter distribution can be rapidly obtained by using a high-rate rotation wet grinder.

A content ratio of products can be controlled by controlling a molar ratio of alcohols as starting materials.

In addition, the catalyst used is a titanate-based catalyst such as tetraisopropyl titanate or tetranormal butyl titanate. For reference, an acid catalyst causes generation of more by-products, easier product discoloration and equipment corrosion, as compared to an organometallic catalyst.

The reaction temperature may range from 180 to 280° C.

The terephthalate composition obtained by the method comprises: 5 to 60% by weight of the terephthalate compound represented by Formula 1; 0.1 to 50% by weight of the terephthalate compound represented by Formula 2; and 30 to 85% by weight of the terephthalate compound represented by Formula 3.

Specifically, the terephthalate composition comprises: 1 to 35% by weight of the terephthalate compound represented by Formula 1; 1 to 35% by weight of the terephthalate compound represented by Formula 2; and 64 to 80% by weight of the terephthalate compound represented by Formula 3.

Furthermore, the plasticizer composition of the present invention comprises: 0.1 to 50% by weight of the plasticizer represented by Formula 1; 0.1 to 50% by weight of the terephthalate compound represented by Formula 2; and 30 to 85% by weight of the terephthalate compound represented by Formula 3, wherein the total weight of the plasticizer, the terephthalate compound of Formula 2 and the terephthalate compound of Formula 3 is 100% by weight, aaaaa wherein the plasticizer composition further comprises 0.1 to 50% by weight of a phthalate compound represented by the following Formula 4.

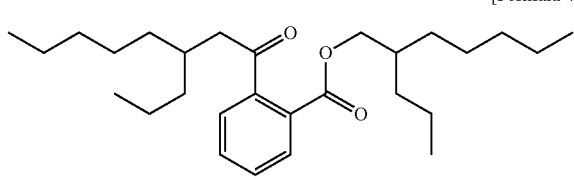

[Formula 4]

Preferably, the plasticizer composition comprises 10 to 40% by weight of the plasticizer represented by Formula 1, 0.1 to 25% by weight of the terephthalate compound of the Formula 2, and 40 to 70% by weight of the terephthalate compound of Formula 3, wherein the total weight of the plasticizer, the terephthalate compound of Formula 2 and the terephthalate compound of Formula 3 is 100% by weight, and the plasticizer composition further comprises 10 to 30% by weight of the phthalate compound represented by Formula 4.

The plasticizer composition may be prepared by mixing the phthalate compound of Formula 4 with the terephthalate composition obtained by the preparation method described above.

The plasticizer composition obtained by the method comprises: 100% by weight of the total weight of a terephthalate composition comprising 0.1 to 50% by weight of the terephthalate compound represented by Formula 1, 0.1 to 50% by weight of the terephthalate compound represented by Formula 2, and 30 to 85% by weight of the terephthalate compound represented by Formula 3; and 0.1 to 50% by weight of dipropyl heptyl phthalate.

Specifically, the plasticizer composition obtained by the method comprises: 100% by weight of the total weight of a terephthalate composition comprising 10 to 40% by weight of the terephthalate compound represented by Formula 1, 0.1 to 25% by weight of the terephthalate compound represented by Formula 2, and 40 to 70% by weight of the terephthalate compound represented by Formula 3; and 10 to 30% by weight of dipropyl heptyl phthalate.

That is, it can be seen that physical properties such as aging resistance, heat resistance and heating loss are poor, when the numbers of carbon atoms constituting the plasticizer composition are 8 and 9, rather than 8 and 10.

When the content of the terephthalate compound represented by Formula 1 is lower than 0.1% by weight, based on the total weight of the composition, tensile strength and elongation retention are poor, and when the content thereof exceeds 50% by weight, migration resistance and heating loss are poor. For example, the content of the terephthalate compound ranges from 10 to 40% by weight.

In addition, when the content of the terephthalate represented by Formula 2 is lower than 0.1% by weight, based on the total weight of the composition, physical properties associated with workability such as absorption speed and melt speed are poor, and when the content thereof exceeds 50% by weight, physical properties associated with heat resistance such as migration resistance and heating loss are considerably low. For example, the content of the terephthalate may range from 0.1 to 25% by weight.

In addition, when the content of the terephthalate represented by Formula 3 is lower than 30% by weight, based on the total weight of the composition, physical properties associated with heat resistance such as migration resistance and heating loss are poor, and when the content thereof exceeds 85% by weight, hardness increases and physical properties associated with workability such as absorption speed and melt speed are considerably deteriorated. For example, the content of the terephthalate ranges from 40 to 70% by weight.

Furthermore, dioctyl phthalate, diethylhexyl phthalate or diisononyl phthalate may be used, instead of the phthalate compound represented by Formula 4. As can be seen from the following examples, physical properties associated with heat resistance such as migration resistance or heating loss are disadvantageously poor when the phthalate compound represented by Formula 4 is used alone, but heat resistance and compatability are improved when the phthalate compound represented by Formula 4 is used in conjunction with the terephthalate compounds of Formulae 1, 2 and 3 described above.

The content of the phthalate compound of Formula 4 is 0.1 to 50% by weight, with respect to 100% by weight of the total weight of the terephthalate compounds represented by Formulae 1, 2 and 3. When the content of the phthalate compound of Formula 4 is lower than 0.1% by weight, the effect of compatability improvement is unsatisfactory and when the content thereof exceeds 50% by weight, the effect of compatability improvement is not potent with respect to the amount of used phthalate compound. For example, the content of the phthalate compound may range from 10 to 30% by weight.

An application example of the plasticizer composition includes, but is not limited to, a heat-resistant resin composition comprising 5 to 100 parts by weight of the plasticizer composition with respect to 100 parts by weight of a resin selected from ethylene vinyl acetate, polyethylene, polypropylene, polyvinyl chloride, polystyrene, polyurethane and a thermoplastic elastomer.

Meanwhile, only the terephthalate compound of Formula 1 separated from the terephthalate composition may be applied to a plasticizer.

Specifically, the present invention also provides a heat-resistant resin composition comprising 5 to 100 parts by weight of the plasticizer of Formula 1 with respect to 100 parts by weight of a resin selected from ethylene vinyl acetate, polyethylene, polypropylene, polyvinyl chloride, polystyrene, polyurethane and a thermoplastic elastomer.

The heat-resistant resin composition may further comprise 0.5 to 7 parts by weight of a stabilizer, 0.5 to 3 parts by weight of a lubricant, and at least one additive such as other plasticizer, a flame retardant, a cross-linking agent or a filler, for example, carbon black.

The heat-resistant resin composition may be applied to compound prescription (treatment) or sheet prescription (treatment). As can be seen from the following examples, the heat-resistant resin composition provides heating loss, heat resistance and compatability enabling application to production of heat-resistant products such as cables (electric wires), automobile interior materials, films, sheets or tubes.

Advantageous Effects

Advantageously, the present invention provides a plasticizer that, when used for a heat-resistant resin composition, improves elongation retention, enhances aging resistance and heat resistance, and exhibits superior tensile strength, tensile strength retention, heating loss or the like before and after heating, thus contributing to enhancement in physical properties of the heat-resistant resin, a plasticizer composition, a heat-resistant resin composition and a method for preparing the same.

BEST MODE

EXAMPLE

Now, the present invention will be described in more detail with reference to the following examples. These examples are provided only to illustrate the present invention and should not be construed as limiting the scope and spirit of the present invention.

Example 1

A reaction mixture of 2.65 mol of terephthalic acid, 1.59 mol of 2-ethyl hexanol and 6.36 mol of 2-propyl heptanol was added to 0.0056 mol of tetraisopropyl titanate as a catalyst in a five-neck round-bottom flask equipped with a temperature sensor, a mechanical stirrer, a condenser, a decanter and a nitrogen purger, followed by reaction at 235° C. for 4 hours.

After reaction, residual alcohol was extracted under reduced pressure, neutralized with sodium bicarbonate, washed with distilled water and dehydrated by reduced-pressure distillation, followed by passing through a filter, to obtain an ester plasticizer composition as the plasticizer composition of the present invention.

GC-mass analysis of the obtained plasticizer demonstrated that the plasticizer comprised the compounds of Formulae 1, 2 and 3 and a weight ratio between the compounds was 25:2:73.

Example 2

The same procedure as in Example 1 was repeated, except that a reaction mixture of 2.65 mol of terephthalic acid, 4.11 mol of 2-ethyl hexanol and 3.84 mol of 2-propyl heptanol was used.

GC-mass analysis of the obtained plasticizer demonstrated that the plasticizer comprised the compound of Formula 1 as a main component and a weight ratio between the compounds of Formulae 1, 2 and 3 was 52:2:46.

Comparative Example 1

The same procedure as in Example 1 was repeated, except that a reaction mixture of 2.65 mol of phthalic acid anhydride, instead of terephthalic acid, and 7.95 mol of isononyl alcohol, instead of 2-ethyl hexanol and 2-propyl heptanol was reacted at 240° C. for 5 hours.

Comparative Example 2

The same procedure as in Example 1 was repeated, except that a reaction mixture of 2.65 mol of terephthalic acid and 7.95 mol of 2-propyl heptanol, containing no 2-ethyl hexanol, was reacted at 220° C. for 5 hours.

Comparative Example 3

The same procedure as in Example 1 was repeated, except that a reaction mixture of 2.65 mol of phthalic acid anhydride, instead of terephthalic acid, and 7.95 mol of isodecyl alcohol, instead of 2-ethyl hexanol and 2-propyl heptanol, was reacted at 220° C. for 5 hours.

Comparative Example 4

The same procedure as in Example 1 was repeated, except that a mixture of 2.65 mol of terephthalic acid, 5.29 mol of 2-ethyl hexanol and 5.29 mol of 2-isononyl alcohol was reacted in the presence of 0.056 mol of tetraisopropyl titanate at 220° C. for 9 hours, and residual alcohol was removed by extraction under reduced pressure.

The reaction mixture was neutralized with sodium bicarbonate, washed with water once, heated under reduced pressure, dehydrated and filtered through a filter material to obtain a plasticizer composition.

GC-mass analysis of the obtained plasticizer demonstrated that the plasticizer comprised 10% of diethylhexyl terephthalate, 54% of ethylhexyl isononyl terephthalate and 36% of diisononyl terephthalate.

Specimens of plasticizers obtained in Examples 1 and 2 and Comparative Examples 1 to 4 were produced in accordance with ASTM D 638. Specifically, 50 parts by weight of a plasticizer, 3 parts by weight of a calcium-zinc stabilizer (LTX-620S) and 0.2 parts by weight of stearic acid were mixed with 100 parts by weight of PVC, followed by molding in a roll mill at 165° C. for 3 minutes, to produce 5 mm sheets. The sheets were pressed into 1 mm sheets by pre-heating at 185° C. for 3 minutes, heating for 3 minutes and cooling for 3 minutes, to produce type-C dumbbell specimens.

Physical properties were tested using the sheets and results are shown in the following Table 1.

<Test Items>

1) Hardness (ASTMD785):

a hardness value was read at seconds after a hardness tester (type "C") needle was completely let down. The hardness was determined as an average of values measured at three spots of each specimen.

2) Tensile Strength and Elongation [ASTM D638]:

Elongation and tensile strength of the specimen on the spot where the specimen was cut were measured using a universal testing machine as a tester after pulling the specimen at a crosshead speed of 200 mm/min. The tensile strength (kgf/cm$^2$) was calculated in accordance with the equation of load (kgf)/thickness (cm)×width (cm) and the elongation (%) was calculated in accordance with the equation of extension/initial length×100.

3) Tensile Strength Retention:

The specimen was allowed to stand in a gear oven at 100° C. for 168 hours, was pulled using a universal testing machine at a cross-head speed of 200 mm/min in accordance with ASTM D638, the spot at which the specimen was cut was measured and tensile strength (kgf/cm$^2$) was calculated in accordance with an equation of load (kgf)/thickness (cm)×width (cm). A tensile strength retention (%) was obtained by dividing a tensile strength obtained by the test in accordance with ASTM D638 at room temperature to the tensile strength after heating (100° C.)

4) Elongation Retention:

The specimen was allowed to stand in a gear oven at 100° C. for 168 hours, was pulled using a universal testing machine as a tester at a cross-head speed of 200 mm/min in accordance with ASTM D638, the spot at which the specimen was cut was measured and elongation (%) was calculated in accordance with the equation of extension/initial length×100. An elongation retention (%) was obtained by dividing an elongation obtained by the test in accordance with ASTM D638 at room temperature by the elongation after heating.

5) Migration Resistance:

An initial weight (Wi) of each specimen was measured to 4 decimal places. The sheet (3 cm×3 cm) was inserted between polystyrene plates in an oven at 80° C. and was allowed to stand for 72 hours while a load of 1 kg was applied thereto, and the specimen was stored in a thermostatic chamber for 4 hours or longer, a weight (Wq) of the specimen was measured and a migration was calculated by the equation (Wi−Wq)/Wi×100.

6) Heating Loss:

An initial weight (Wi) of each specimen was measured to 4 decimal places. The specimen was set using a clamp in an oven at 121° C. After 72 hours, the specimen was maintained in a thermostatic chamber for 4 hours or longer, a weight (Wo) of the specimen was measured, and heating loss was calculated by the equation of (Wi−Wo)/Wi×100.

TABLE 1

| | Items | | Ex. 1 | Ex. 2 | Comp. Ex. 1 | Comp. Ex. 2 | Comp. Ex. 3 | Comp. Ex. 4 |
|---|---|---|---|---|---|---|---|---|
| Physical properties | Hardness | | 94.5 | 93.5 | 87.5 | 98.5 | 89 | 90 |
| | Room temperature | Elongation (%) | 200.0 | 198.6 | 171.6 | 215.3 | 193.5 | 181.8 |
| | | Tensile strength (kg/cm$^2$) | 285.7 | 240.0 | 256.8 | 218.9 | 251.1 | 275.1 |
| | After heating | Elongation (%) | 199.7 | 193.9 | 177.6 | 218.4 | 196.5 | 179.8 |
| | | Tensile strength (kg/cm$^2$) | 204.4 | 182.1 | 191.8 | 193.2 | 196.1 | 207.8 |
| | | Tensile strength retention (%) | 100 | 98 | 103.4 | 101 | 101 | 98.9 |
| | | Elongation retention (%) | 84 | 75 | 74.6 | 87 | 78 | 75.5 |
| | Migration resistance (%) | | 0.3 | 0.2 | 0.2 | 0.5 | 0.2 | 0.1 |
| | Heating loss (%) | | 1.4 | 3.7 | 5.3 | 0.5 | 4.4 | 3.9 |

As can be seen from the results shown in Table 1 above, Examples 1 and 2 exhibited superior physical properties associated with heat resistance. Specifically, Examples 1 and 2 exhibited superior heating loss among physical properties associated with heat resistance, as compared to Comparative Examples 3 and 4. In addition, as a result of comparison of Examples 1 and 2 with Comparative Examples 1 and 2, it can be seen that Examples 1 and 2 exhibited superior elongation retention, migration resistance and heating loss.

Example 3

The same process as in Example 1 was repeated, except that a compound represented by the following Formula 4 was added to the composition obtained in Example 1 such that a content of the compound of Formula 4 after mixing was 10% by weight.

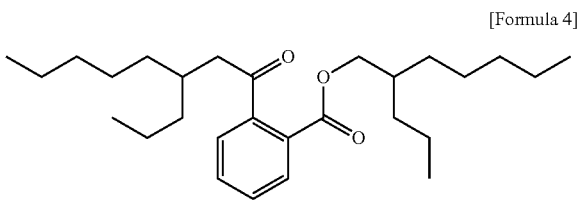 [SMILES: CCCCCC(CCC)COC(=O)c1ccccc1C(=O)CC(CCC)CCCCC]

[Formula 4]

Example 4

The same process as in Example 3 was performed, except that the compound of Formula 4 was added to the composition in Example 3 such that the content of the compound of Formula 4 after mixing was 30% by weight.

Comparative Example 5

The same process as in Example 3 was performed, except that the compound of Formula 4 was added to the composition in Example 3 such that the content of the compound of Formula 4 after mixing was 60% by weight.

Comparative Example 6

The same process as in Example 3 was performed, except that the compound of Formula 4 was not added to the composition in Example 3.

Comparative Example 7

2.65 mol of phthalic acid anhydride was reacted with 8 mol of 2-propyl heptanol in the presence of 0.056 mol of tetraisopropyl titanate at 220° C. for 3.5 hours and residual alcohol was removed by extraction under reduced pressure.

The resulting mixture was neutralized with sodium bicarbonate, washed with water once, heated under reduced pressure, dehydrated and filtered through a filtering material to obtain a plasticizer composition.

Comparative Example 8

2.65 mol of terephthalic acid, 4 mol of 2-ethyl hexanol and 4 mol of 2-propyl heptanol were reacted in the presence of 0.056 mol of tetraisopropyl titanate at 220° C. for 9 hours and residual alcohol was removed by extraction under reduced pressure.

The resulting mixture was neutralized with sodium bicarbonate, washed with water once, heated under reduced pressure, dehydrated and filtered through a filtering material to obtain a plasticizer composition.

GC-mass analysis of the obtained plasticizer demonstrated that the plasticizer comprised 10% of diethylhexyl terephthalate, 54% of ethylhexyl isononyl terephthalate and 36% of diisononyl terephthalate.

Comparative Example 9

2.65 mol of phthalic acid anhydride was reacted with 8 mol of isodecanol in the presence of 0.056 mol of tetraisopropyl titanate at 235° C. for 5 hours and residual alcohol was removed by extraction under reduced pressure.

The resulting mixture was neutralized with sodium bicarbonate, washed with water once, heated under reduced pressure, dehydrated and filtered through a filtering material to obtain a plasticizer composition.

Specimens of plasticizers obtained in Examples 3 and 4 and Comparative Examples 5 to 9 were produced in accordance with ASTM D638. Specifically, 50 parts by weight of a plasticizer, 3 parts by weight of an epoxylated soybean oil and 2.5 parts by weight of a Ba—Zn stabilizer were mixed with 100 parts by weight of PVC, followed by molding in a roll mill at 160° C. for 4 minutes, to produce 5 mm sheets. The sheets were pressed at 180° C. under low pressure for 3 minutes and at 180° C. under high pressure for 2.5 minutes to obtain 1 mm sheets.

Hardness (ASTM D785), tensile strength, elongation [ASTM D638], migration resistance and heating loss of the respective sheets were measured in the same manner as in Table 1. In addition, plasticizer absorption speed was obtained by measuring a time at which 200 g of a plasticizer was absorbed at 77° C. in 400 g of PVC during rotation at 60 rpm. Results are shown in the following Table 2.

TABLE 2

| | Items | Ex. 3 | Ex. 4 | Comp. Ex. 5 | Comp. Ex. 6 | Comp. Ex. 7 | Comp. Ex. 8 | Comp. Ex. 9 |
|---|---|---|---|---|---|---|---|---|
| Physical properties | Hardness | 74.5 | 73 | 72.5 | 76.5 | 68 | 68 | 71 |
| | Tensile strength (kg/cm$^2$) | 159 | 157 | 154 | 160 | 152 | 169 | 152 |
| | Elongation (%) | 402 | 400 | 398 | 402 | 396 | 403 | 392 |
| | Migration resistance (%) | 0.76 | 0.78 | 0.85 | 0.75 | 0.88 | 1.05 | 0.74 |
| | Heating loss (%) | 1.40 | 1.49 | 1.89 | 1.36 | 2.21 | 3.23 | 1.35 |
| | Absorption speed(sec) | 610 | 590 | 570 | 740 | 544 | 470 | 525 |

As can be seen from the results shown in Table 2, Examples 3 and 4 exhibited superior physical properties associated with heat resistance as well as compatability. Specifically, Examples 3 and 4 exhibited superior migration resistance and heating loss, as physical properties associated with heat resistance, as compared to Comparative Examples 7 and 8, and exhibited superior tensile strength and elongation, as compared to Comparative Example 9. In addition, as a result of comparison of Examples 3 and 4 with Comparative Example 6, it can be seen that compatability is improved through addition of the compound of Formula 4.

The invention claimed is:

1. A plasticizer composition comprising:
   1 to 35% by weight of the plasticizer represented by Formula 1;
   1 to 35% by weight of a terephthalate compound represented by Formula 2; and
   64 to 80% by weight of a terephthalate compound represented by Formula 3,

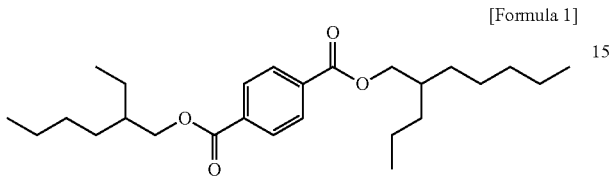
[Formula 1]

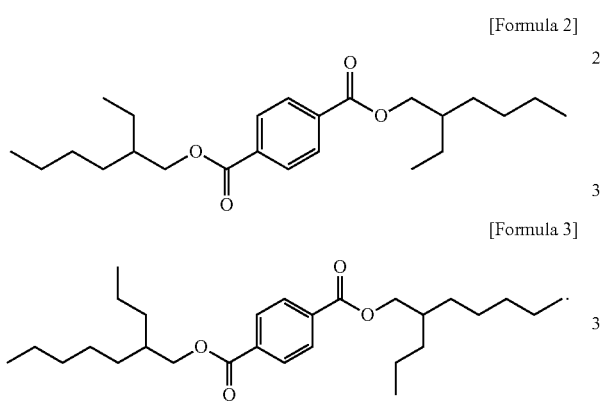
[Formula 2]

[Formula 3]
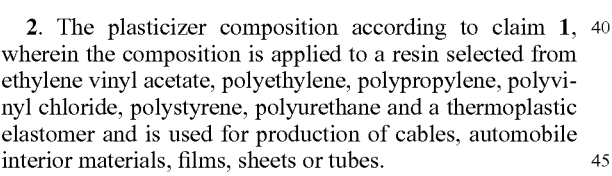

2. The plasticizer composition according to claim 1, wherein the composition is applied to a resin selected from ethylene vinyl acetate, polyethylene, polypropylene, polyvinyl chloride, polystyrene, polyurethane and a thermoplastic elastomer and is used for production of cables, automobile interior materials, films, sheets or tubes.

3. A heat-resistant resin composition comprising 5 to 100 parts by weight of the plasticizer composition according to claim 1, with respect to 100 parts by weight of a resin selected from ethylene vinyl acetate, polyethylene, polypropylene, polyvinyl chloride, polystyrene, polyurethane and a thermoplastic elastomer.

4. The heat-resistant resin composition according to claim 3, wherein the heat-resistant resin composition is applied to production of cables, automobile interior materials, films, sheets or tubes through compound prescription or sheet prescription.

5. A plasticizer composition comprising:
   0.1 to 50% by weight of the plasticizer represented by Formula 1;
   0.1 to 50% by weight of a terephthalate compound represented by Formula 2; and
   30 to 85% by weight of the terephthalate compound represented by Formula 3,
   wherein the total weight of the plasticizer, the terephthalate compound of Formula 2 and the terephthalate compound of Formula 3 is 100% by weight, and
   wherein the plasticizer composition further comprises 10 to 30% by weight of a phthalate compound represented by Formula 4,

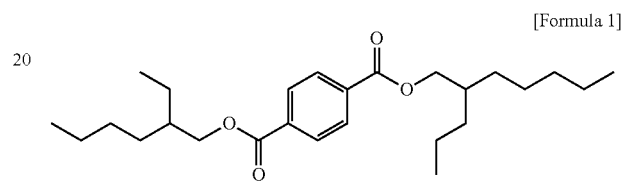
[Formula 1]

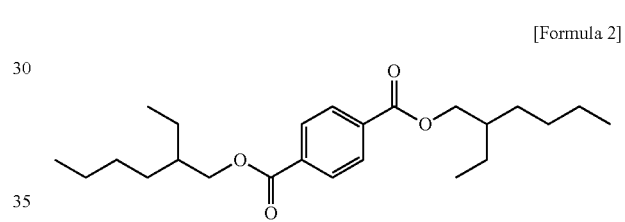
[Formula 2]

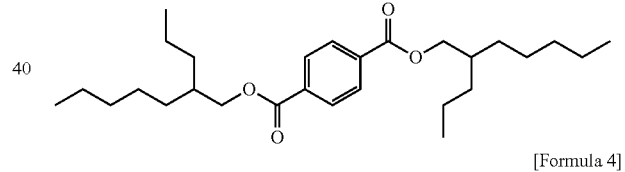
[Formula 3]

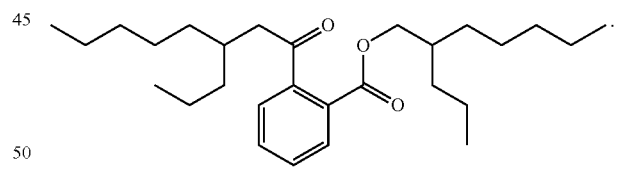
[Formula 4]

* * * * *